US00PP27638P3

(12) United States Plant Patent
Dalton et al.

(10) Patent No.: US PP27,638 P3
(45) Date of Patent: Jan. 31, 2017

(54) ***DICENTRA* PLANT NAMED 'WHITE GOLD'**

(50) Latin Name: *Dicentra spectabilis (Lamprocapnos spectabilis)*
Varietal Denomination: White Gold

(71) Applicants: Margaret Dalton, Middle Grove, NY (US); James Dalton, Middle Grove, NY (US)

(72) Inventors: Margaret Dalton, Middle Grove, NY (US); James Dalton, Middle Grove, NY (US)

( * ) Notice: Subject to any disclaimer, the term of this patent is extended or adjusted under 35 U.S.C. 154(b) by 77 days.

(21) Appl. No.: 14/545,245

(22) Filed: Apr. 13, 2015

(65) Prior Publication Data
US 2016/0302344 P1 Oct. 13, 2016

(51) Int. Cl.
*A01H 5/02* (2006.01)

(52) U.S. Cl.
USPC ..... Plt./426

(58) Field of Classification Search
USPC ..... Plt./426
See application file for complete search history.

*Primary Examiner* — Keith Robinson
(74) *Attorney, Agent, or Firm* — Klarquist Sparkman, LLP; Sheree Lynn Rybak

(57) ABSTRACT

A new and distinct form of *Dicentra* plant characterized by soft, golden to yellow green foliage, large white flowers, and excellent vigor.

1 Drawing Sheet

Botanical denomination: *Dicentra spectabilis* (*Lamprocapnos spectabilis*).
Variety designation: 'White Gold'.

BACKGROUND OF THE INVENTION

The present invention relates to a new and distinct cultivar of *Dicentra spectabilis* (*Lamprocapnos spectabilis*), of the family Papaveraceae, and given the cultivar name, 'White Gold'. This plant originated as a chance seedling growing in a garden in Middle Grove, N.Y. The discovery was made in spring of 2010.

This new cultivar is uniquely characterized by:
1. soft, golden to yellow green foliage,
2. large white flowers, and
3. excellent vigor.

Compared to *Dicentra spectabilis* 'Alba', an unpatented plant, the new cultivar has golden to yellow green leaves rather than green leaves.

Compared to *Dicentra spectabilis* 'Gold Heart', an unpatented plant, the new cultivar has white rather than pink and white flowers.

The new variety has been reproduced only by asexual propagation. Each of the progeny exhibits identical characteristics to the original plant. Asexual propagation by micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows an eighteen-month-old *Dicentra* 'White Gold' in the garden in a two gallon container in early April in Canby, Oreg.

FIG. 2 shows a close up of the same plant.

DETAILED PLANT DESCRIPTION

The following is a detailed description of the new *Dicentra* cultivar based on observations of eighteen-month-old specimens grown in a covered area outside in two gallon containers in April in Canby, Oreg. Canby is Zone 8 on the USDA Hardiness map. Temperatures range from a high of 95° F. in August to 32° F. in January. Normal rainfall in Canby is 42.8 inches per year. The color descriptions are all based on The Royal Horticultural Society Colour Chart, 5$^{th}$ edition, 2007.

Plant:
- *Type*.—Herbaceous perennial.
- *Form*.—Clumping.
- *Cold hardiness*.—USDA Zone 3 to 9.
- *Size*.—Grows to 34 cm tall and 70 cm wide.
- *Vigor*.—Excellent.

Stem:
- *Size*.—Grows to 35 cm long and 7 mm wide at the base.
- *# Stems*.—6.
- *Strength*.—Strong.
- *Branching*.—Basal with stem leaves and terminal and lateral racemes.
- *Internodes*.—4 cm to 7 cm long.
- *Color*.—Yellow Green 145B.

Leaf:
- *Type*.—Pinnately compound with ternately compound leaflets.
- *Arrangement*.—Alternate.
- *Quantity*.—Good.
- *Shape*.—Broadly ovate to triangular in outline, leaflets usually obovate.
- *Lobing/division*.—Leaflets 3 cleft to parted and 2 to 4 lobed with entire margins, ovate to broadly ovate, apiculate tips, cuneate bases, glabrous on both sides, leaflet size variable, grow to 8 cm long and 4 cm wide.

*Blade size*.—Grows to 20.5 cm long and 18 cm wide.

*Venation*.—Pinnate.

*Surface texture*.—Glabrous on both sides.

*Petiole description*.—Grows to 8 cm long and 3 mm wide, glabrous, Yellow Green 145C.

*Leaf/leaflet color*.—Young leaves (including veins) top side closest to Yellow Green N144A, bottom side 147D; older leaves (including veins) topside closest to Yellow Green N145A, bottom side 147D.

*Stipules*.—None.

Inflorescence:

*Type*.—Axillary and terminal racemes.

*Number of flowers*.—3 to 12 per raceme, increasing with older stems.

*Number of racemes in first spring flush*.—12.

*Size*.—Grows 0 cm to 3 cm long and to 3.5 cm wide.

*Peduncle description*.—Grows 6 cm to 16 cm long and to 3 mm wide, glabrous, Yellow Green 145B, medium strength.

*Pedicel description*.—5 mm to 7 mm long, less than 1 mm wide, Yellow Green 145B.

*Bloom period*.—April to June in Canby, Oreg.

Flower bud:

*Size*.—Grow to 20 mm long and 14 mm wide at the widest point prior to opening.

*Description*.—Oblong with the base wider than the tip and heart-shaped, self-cleaning.

*Color*.—White NN155D on heart shaped top, tip White NN155D with spot Green Yellow 1A.

Flower:

*Type*.—Zygomorphic.

*Corolla description*.—Pendulous, 22 mm long and 26 mm wide, heart-shaped on bottom half, laterally compressed, 4 petals in 2 opposed pairs; outer petal pair pouched at the base forming the heart shape, reflexed on top ⅓ and cupped at tip, each 17 mm long and spreading 5 mm wide with reflexed limb 6 mm long and 3 mm wide, margins entire, tip acute, glabrous and White NN155D inside and out; inner petal pair tongue shaped and connected at the tip, 22 mm long (5 mm extruding) and to 9 mm wide, with convex inner face and crested apex; margins entire, tip apiculate; inside and outside glabrous and White NN155D with spot Green Yellow 1A about 3 mm long and 2 mm wide just above outer petal pair.

*Calyx description*.—2 sepals, scale line, not seen.

*Pistil description*.—One, linear and 19 mm long, Yellow Green 145B, ovary 11 mm long and 1.5 mm wide, style 7 mm long, stigma is double arrow-shaped, 1 mm wide.

*Stamen description*.—6 in number, compound with 3 partially fused sections in each inner petal, 21 mm long, filaments 20 mm long and to 1.5 mm wide, White NN155D, anthers 1 mm long, ovoid, Green Yellow 1D, pollen Yellow 13B, in moderate amounts.

*Fragrance*.—None.

*Lastingness*.—A raceme blooms for about 4 weeks on the plant.

Fruit: A lanceolate capsule, dehiscent with 2 valves, grows to 22 mm long and 3.5 mm wide, Yellow Green 145A, about 3 seeds per fruit.

Seed: Arrilate, round, 1.5 mm wide, Black 202A.

Pest and disease tolerance: The new cultivar is typical to the genus. No problems have been found in Canby, Oreg.

We claim:

1. A new and distinct form of *Dicentra* plant as hereby illustrated and described.

* * * * *

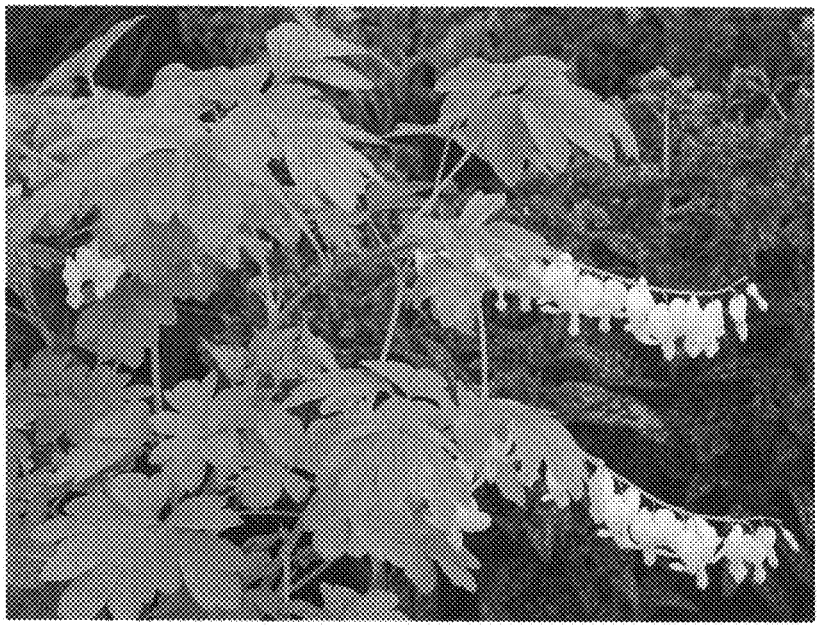

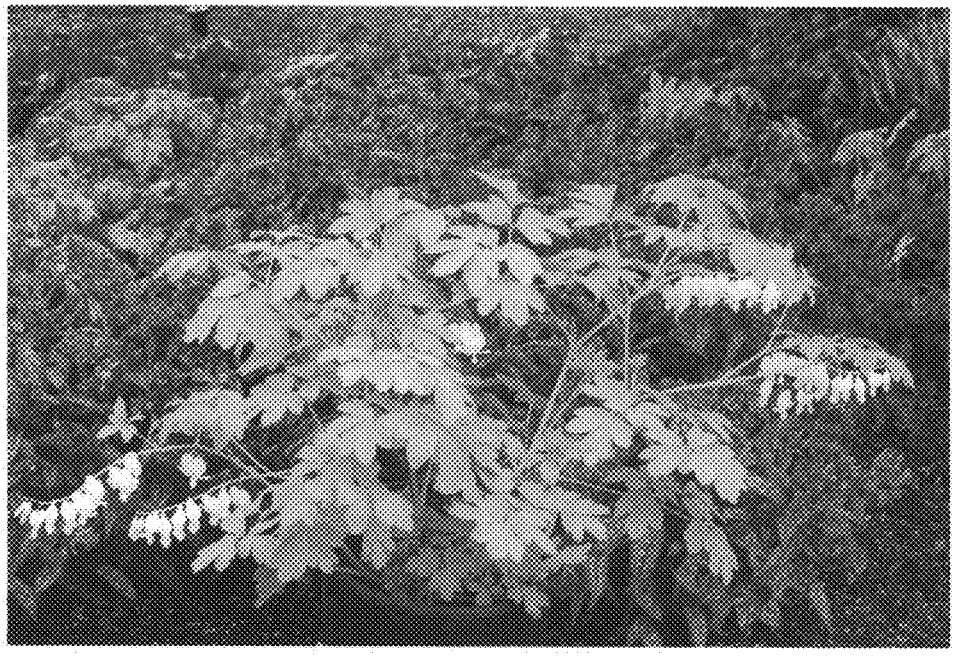
FIG. 1 above, FIG. 2 below